United States Patent
Sherman

[11] Patent Number: 5,869,971
[45] Date of Patent: Feb. 9, 1999

[54] METHOD AND APPARATUS FOR RATIOMETRIC MEASUREMENT OF HEMATOCRIT

[75] Inventor: Marshall L. Sherman, Cardiff By the Sea, Calif.

[73] Assignee: SenDx Medical, Inc., Carlsbad, Calif.

[21] Appl. No.: 649,525

[22] Filed: May 17, 1996

[51] Int. Cl.⁶ .................................................. G01N 27/06
[52] U.S. Cl. .......................... 324/439; 324/692; 324/71.1
[58] Field of Search ................................... 324/439, 442, 324/692, 693, 71.1

[56] References Cited

U.S. PATENT DOCUMENTS

| | | | |
|---|---|---|---|
| 3,772,591 | 11/1973 | Louder et al. | 324/446 |
| 3,812,425 | 5/1974 | Miller | 324/71.1 |
| 3,922,598 | 11/1975 | Steuer et al. | 324/442 |
| 4,068,169 | 1/1978 | Angel et al. | 324/71.1 |

FOREIGN PATENT DOCUMENTS 0 256 324   7/1987   European Pat. Off. ....... G01N 27/06

OTHER PUBLICATIONS

Teyssedou et al., "Impedance probe to measure local void fraction profiles", Review of Scientific Instruments 59 (1988) Apr., No. 4, NY USA, pp. 631–638.

*Primary Examiner*—Glenn W. Brown
*Attorney, Agent, or Firm*—Baker, Maxham, Jester & Meador

[57] ABSTRACT

A method and apparatus for measuring resistance of a blood sample in order to determine the hematocrit of that blood sample. The present invention makes a direct ratiometric measurement. That is, the alternating current that flows through the sample is directly measured by applying that alternating current to an integrator which converts the current to a D.C. voltage which is directly proportional to the applied current.

18 Claims, 2 Drawing Sheets

METHOD AND APPARATUS FOR RATIOMETRIC MEASUREMENT OF HEMATOCRIT

BACKGROUND OF THE INVENTION

1. Field of the Invention

This invention relates to medical diagnostic equipment, and more particularly to blood analyzers for measuring hematocrit value of a blood sample.

2. Description of Related Art

Measurement of hematocrit (i.e., volume of red blood cells per unit volume of whole blood) is useful for monitoring, diagnosing, and otherwise determining the health and status of a medical patient. One method for measuring hematocrit is to directly count the number of red blood cells using a conventional microcentrifuge and modem cell-counting cytometry methods. However, such methods are not amenable to the design of convenient or continuous bedside monitoring instruments. Rather, an indirect method in which blood conductivity ($1/R_{blood}$) is measured is preferred for determining hematocrit in order to make it possible to determine hematocrit at bedside. It is well known that the conductivity of a blood sample varies as a function of its hematocrit value. It is also known that other blood components must be taken into account when calculating hematocrit based upon the conductivity of a blood sample. Currently, bridge circuits are used to determine the resistance ($R_{blood}$) of a blood sample. A bridge circuit determines resistance by comparing an unknown resistance (i.e., $R_{blood}$) with a known resistance.

FIG. 1 is an illustration of a Wheatstone bridge circuit commonly used to determine the resistance ($R_{blood}$) of a blood sample. The bridge circuit comprises two fixed resistors $R_a$, $R_b$ with known values. The values of these resistors $R_a$, $R_b$ must be known to a very high precision in order to accurately determine the value of the resistance ($R_{blood}$) of a blood sample. One terminal of each of the resistors $R_a$, $R_b$ is coupled together at node 100. A "zero-center" current meter 104 is coupled between the other terminal of each of the known resistors $R_a$, $R_b$ at nodes 101, 102. Also coupled to the node 102 is a first terminal of the hematocrit sensor. The hematocrit sensor is shown in FIG. 1 as an equivalent resistor having a resistance $R_{blood}$. The first terminal of the hematocrit sensor is placed in contact with the blood sample to be measured. A second terminal of the hematocrit sensor which is also in contact with the blood sample is coupled to a node 103. A high precision potentiometer 105 having a resistance $R_{pot}$ is coupled between nodes 101 and 103 and a voltage source 106 is placed across nodes 100 and 103. It is well known that when no current flows through the current meter 104, the value of the unknown resistance $R_{blood}$ is equal to:

$$R_{pot}(R_b/R_a)$$

However, there are a number of disadvantages to using such a bridge circuit to measure hematocrit. It is typically desirable to have the resistance measurement device interface with a microprocessor or other programmable device in order to allow additional calculations to be performed, such as adjusting the measured resistance to account for electrolytes in the blood, and to allow data to be compiled, logged, and reported. Also, such bridge circuits require adjustments to be made to the potentiometer to set the bridge to null, and calibrations to be made to ensure the accuracy of the bridge circuit (i.e., the accuracy of the known resistances). Furthermore, such bridge circuits require compensation for both temperature and voltage. Still further, the voltage source 106 must be very stable. In addition, such bridge circuits typically require a great deal of space and are expensive due to the number of high precision components required. Therefore, in general, bridge circuits are difficult and expensive to make accurate, inherently instable over long periods of time, and require close tolerance components.

Accordingly, it would be desirable to provide a method and apparatus for measuring the conductivity (or resistance) of a blood sample for use in a hematocrit measurement device which is stable over long periods of time, is inexpensive, can be fabricate in relatively small space, which does not require regular calibration and adjustment, and which can easily interface with a microprocessor or other digital device.

SUMMARY OF THE INVENTION

The present invention is a method and apparatus for measuring resistance of a blood sample in order to determine the hematocrit of that blood sample. The present invention makes a direct ratiometric measurement. That is, the alternating current that flows through the sample is directly measured by applying that alternating current to an integrator which converts the current to a direct current voltage which is directly proportional to the applied current.

The present invention includes a programmable logic device which controls an enable function, generates a first square wave signal, a second square wave signal which is 90 degrees out-of-phase with the first square wave signal, and a third square wave signal which is 270 degrees out-of-phase with the first square wave signal. A filter shapes the first square wave signal into a sinusoidal wave with a 90 degree phase shift at the output. A first switch allows the circuit of the present invention to be disabled by disconnecting the circuit (including the hematocrit sensor) from the A.C. voltage source which drives the circuit. Additional switches half-wave rectify the A.C. current that flows through the blood sample. These switches are synchronized to the output of the filter and cause the negative going pulses to be coupled to ground, and the positive going pulses to be coupled to an integrator. The output of the integrator is a D.C. voltage that is directly proportional to the current that flows through the sample. In accordance with the present invention, the ratio of the voltage which is present at the output when the hematocrit sensor is emersed in a reference solution with respect to the voltage that is present at the output when the hematocrit sensor is emersed in an analyte is a unit-less value that is directly used to calculate the hematocrit of the reference solution without the need to determine the resistance through the hematocrit sensor or the current flowing therethrough.

BRIEF DESCRIPTION OF THE DRAWING

The objects, advantages, and features of this invention will become readily apparent in view of the following description, when read in conjunction with the accompanying drawing, in which.

Like reference numbers and designations in the various drawings refer to like elements.

DETAILED DESCRIPTION OF THE INVENTION

Throughout this description, the preferred embodiment and examples shown should be considered as exemplars, rather than limitations on the present invention.

Figure 1:
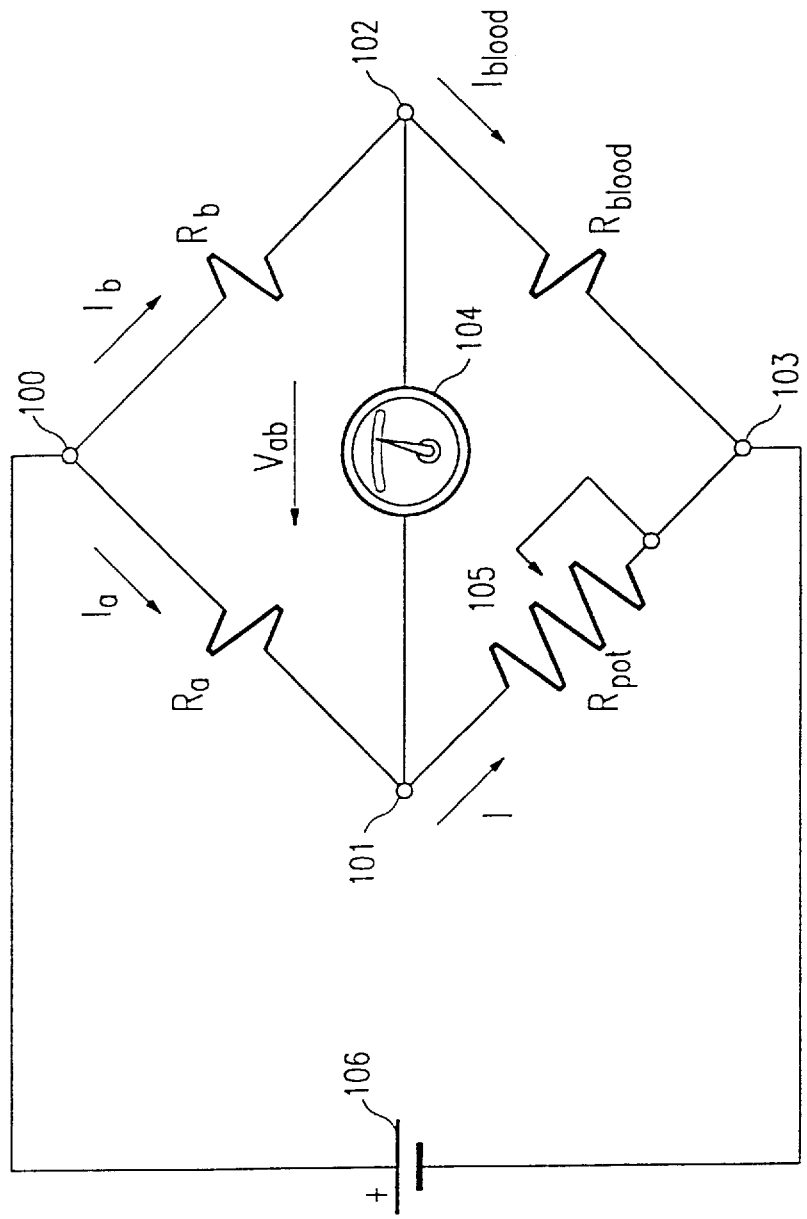
FIG. 1 is an illustration of a prior art Wheatstone bridge used to measure the resistance of a blood sample.
Figures 2, 3:
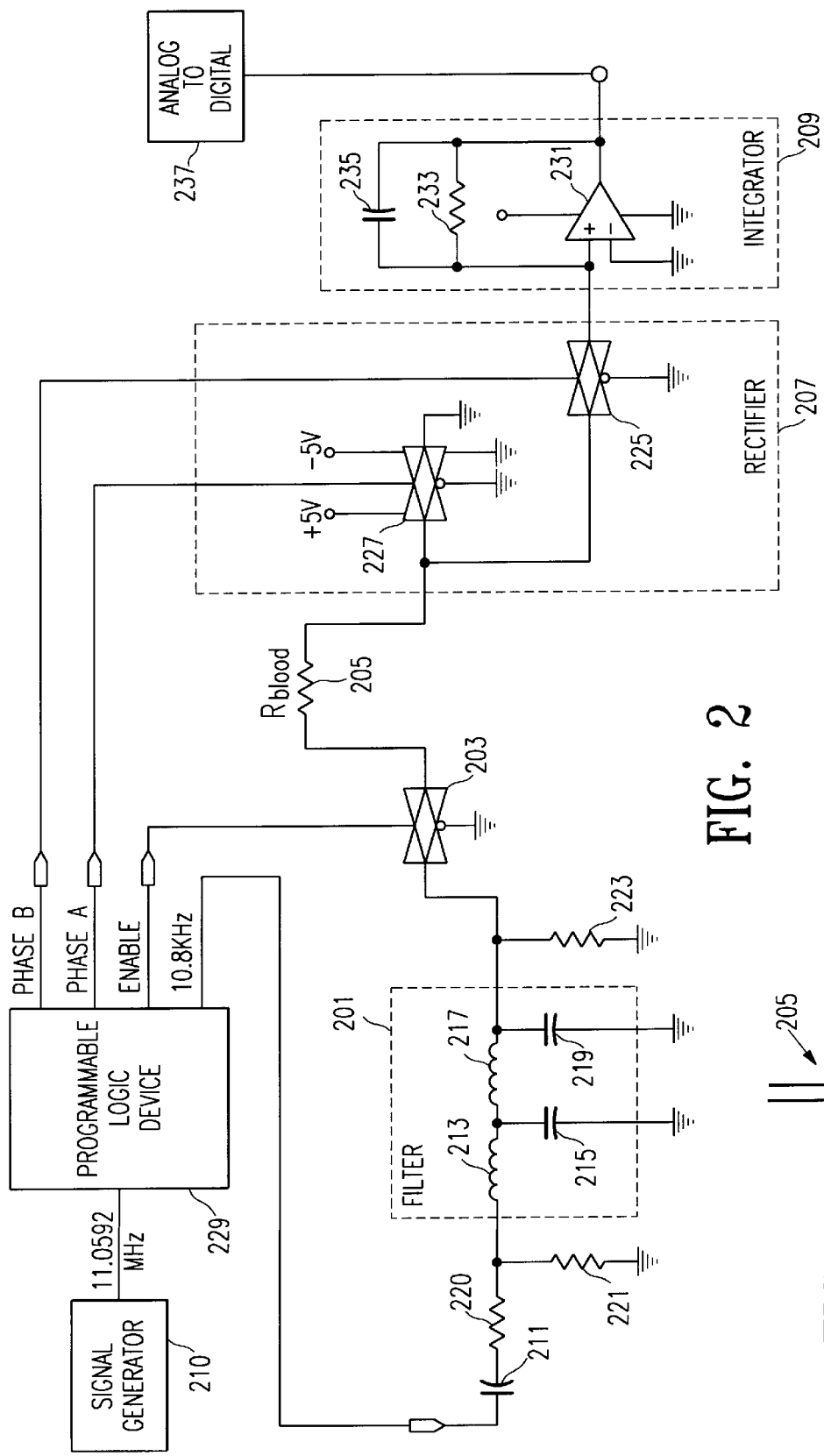
FIG. 2 is a electrical schematic of the circuit of the present invention used to measure conductivity of a blood sample in order to determine the hematocrit of the blood sample.
FIG. 3 is a diagrammatic illustration of a pair of spaced electrodes to measure conductivity of a blood sample.

The present invention is a method and apparatus for measuring the conductivity of a blood sample in order to determine the hematocrit of the sample. FIG. 2 is an electrical schematic of the conductivity measurement circuit of the present invention. The conductivity measurement circuit of the present invention preferably comprises five elements: (1) a filter 201; (2) a switch 203; (3) a hematocrit sensor 205; (4) a rectifier 207 and (5) an integrator 209.

In accordance with one embodiment of the present invention, a square wave signal is generated having a frequency of 11.0592 MHz by a drive signal source 210. The drive signal source may be a crystal frequency generator, for example. That signal is then divided by 1024 to a frequency of 10.8 kHz. In accordance with one embodiment of the present invention, the division of the 11.0592 MHz signal is performed by a programmable logic device 229. The 10.8 kHz signal is then applied to a coupling capacitor 211, which removes any D.C. offset which might be present. A pair of resistors 220, 221 establish the input impedance of the filter 201. The filter 201 shown in FIG. 2 has 4 poles established by a first inductor 213, a first capacitor 215, a second inductor 217, and a second capacitor 219. It should be understood that any filter may be used to remove the odd harmonics from the square wave signal to provide a sinusoidal signal at the output of the filter 201. A resistor 223 is coupled in parallel to the output of the filter 201 to establish the output impedance at the filter output.

The filter output is coupled to the switch 203. The switch 203 allows the sinusoidal output signal from the filter to be selectively connected and disconnected from the hematocrit sensor 205. When disconnected, no current flows through the hematocrit sensor 205, effectively disabling the circuit. In one embodiment of the present invention, the switch 203 is a field effect transistor switch, such as part number 74HC3416 available from Motorola. The enable/disable function is preferably controlled by the programmable logic device 229, which is coupled to the switch 203. In the one embodiment of the present invention, the programmable logic device is the same device that divides the 11.0592 MHz signal by 1024.

If the switch 203 is enabled, the signal applied to the input of the switch is coupled to the input to the hematocrit sensor 205 via the output of the switch 203. The output from the hematocrit sensor 205 is coupled to two additional switches 225, 227 which comprise the half wave rectifier 207. The first of these switches 225 selectively couples the output of the hematocrit sensor 205 to the integrator 209. The control input to the switch 225 is coupled to a signal "PhaseB" which is equal in frequency to the 10.8 kHz signal applied to the input filter, and in the case of the circuit shown in FIG. 2, is 90 degrees out-of-phase with that signal. The 90 degree phase shift compensates for a 90 degree phase shift imposed upon the 10.8 kHz signal by the filter 201 and results in the PhaseB control signal being in phase with the 10.8 kHz signal. It should be understood that the phase shift between the signal input to the filter 201 and the PhaseB control signal is preferably equal to the phase shift imposed by the filter 201.

In the preferred embodiment of the present invention, the PhaseB signal is derived from the same 11.0592 MHz signal that is used to derive the 10.8 kHz signal within the programmable logic device 229 by dividing the 11.0592 signal by 512, then inverting the resulting signal and then dividing the inverted signal by 2. Preferably, the same divider circuitry may be used to divide by 512 to generate both the 10.8 kHz input to the filter 201 and the PhaseB control signal. In the case of the 10.8 kHz input signal, the output from the 512 divider circuit is simply divided by two, whereas in the case of the PhaseB signal, the signal is first inverted and then divided by 2. Since the control signal PhaseB is synchronized with the input to the switch 225, the switch will be "turned on" (i.e., the input will be coupled through to the output) during the negative current phase (i.e., when current is flowing from the switch 225 to the hematocrit sensor 205), and will be "turned off" (i.e., the input will be disconnected from the output) during the positive current phase (i.e., when the current is flowing from the hematocrit sensor 205 to the switch 225). The integrator 209 smooths and inverts the output from the switch 225 to provide a D.C. output which is directly proportional to the current that flows through the hematocrit sensor 205. In accordance with the embodiment shown in FIG. 2, the integrator is an operational amplifier 231 in which a feedback circuit between the output and the inverting input includes a parallel coupled resistance 233 and capacitance 235. The non-inverting input is coupled to ground.

The output from the second switch 227 is coupled to ground. The second switch 227 is controlled by a control signal "PhaseA" that is 180 degrees out-of-phase with the PhaseB signal, such that the output from the hematocrit sensor 205 is grounded during the positive current phase (i.e., when current is flowing from the switch 225 to the hematocrit sensor). By grounding the output from the hematocrit sensor 205 during the positive current phase, the sensor 205 is balanced and thus produces no D.C. offset.

In accordance with the present invention, a first measurement is made with the hematocrit sensor 205 emersed in a calibrant, such as a saline solution. The calibrant provides a reference. After establishing the reference with the calibrant, the hematocrit sensor 205 is emersed in the sample to be measured. Once the measurements of both the calibrant and the sample have been taken, the hematocrit value can be directly calculated (assuming that the electrolyte concentrations are also known, preferably by an independent concurrent measurement).

Those skilled in the art will be aware that the relationship between hematocrit of a blood sample and specific resistance of a blood sample is:

$$H = a \ln \phi - b$$

where a and b are "cell constants" which depend upon the spacing of the hematocrit electrodes, the geometry of each such electrode, and the volume of the fluid sample through which current will flow. Also, $\phi = R_{blood}/R_{cal}$; where $R_{blood}$ is the resistance measured through the sample and $R_{cal}$ is the resistance measured through the calibrant. Since the voltage that is output from the integrator 209 is directly proportional to the resistance of either the blood sample or the calibrant sample, depending upon in which fluid the hematocrit sensor is emersed, the ratio of the voltages output from the integrator 209 will be equal to $\phi$. Accordingly, no direct knowledge of the resistance of the hematocrit sensor is required in order to determine the hematocrit value of the blood sample. This is advantageous, since there are several variables which must be known in order to determine the resistance of the hematocrit sensor.

The hematocrit sensor 205 is preferably a pair of platinum electrodes, such as shown in FIG. 3, having a diameter of 0.040 inches and spaced approximately 0.5 cm apart. Once the geometry and materials used to form the electrodes of the hematocrit sensor are determined, the values of a and b can be determined by empirical studies of the operation of the sensor in response to solutions of differing hematocrit values. In an alternative embodiment, other configurations of electrodes and other materials may be used with appropriate adjustments being made to the values of a and b.

In accordance with one embodiment of the present invention, the output from the integrator 209 is digitized by a conventional analog to digital converter 237. The digital value which corresponds to the output from the integrator 209 when the hematocrit sensor is emersed in the analyte is divided by the digital value that corresponds to the output from the integrator 209 when the hematocrit sensor is emersed in the reference solution.

SUMMARY

The present invention provides a method and apparatus for measuring the conductance of a blood sample using a direct ratiometric measurement. That is, the ratio of the voltage that is output from the integrator of the present invention when the hematocrit sensor is emersed in a reference solution to the voltage that is output when the hematocrit sensor is emersed in the analyte is used directly to calculate the hematocrit of the analyte. Neither the resistance of the hematocrit sensor, nor the current that flows through the hematocrit sensor need be determined. The apparatus of the present invention does not require any adjustment or calibration, interfaces easily with a digital device, such as a microprocessor, does not require compensation for temperature or voltage levels, can be fabricated easily within an integrated circuit, can be fabricated using inexpensive components, and can be very easily mass produced.

A number of embodiments of the present invention have been described. Nevertheless, it will be understood that various modifications may be made without departing from the spirit and scope of the invention. For example, while the filter 201 is described and shown as a 4-pole low pass filter, any filter which passes the fundamental frequency and filters out the odd harmonics in order to output a sinusoidal output signal may be used. In addition, in one alternative embodiment of the present invention, the filter may be omitted if the input to the current circuit is a sinusoid. Furthermore, in accordance with one embodiment of the present invention, the enable switch 203 may be omitted. Still further, any half-wave rectifier circuit may be used in place of the switches 225, 227. However, the use of a switched rectifier eliminates the voltage drop that results when conventional unidirectional components, such as diodes, are used to perform the rectification. Such voltage drops adversely effect the hematocrit measurement. Furthermore, most unidirectional components are temperature sensitive, thus requiring temperature compensation circuitry to ensure accuracy in the hematocrit measurement. Also, while the integrator 209 is described as comprising an operational amplifier configured as an integrator, any circuit may be used which operates as an integrator in order to provide a smooth D.C. output which is proportional to the A.C. current that flows through the hematocrit sensor 205. Furthermore, the control signals PhaseA, and PhaseB may be generated by any means which results in signals that are 180 degrees out-of-phase from each other, and in phase with the driving signal at the output from the filter 201. For example, a programmable delay and inverter may be used to generate the control signals PhaseA and PhaseB. Accordingly, it is to be understood that the invention is not to be limited by the specific illustrated embodiments, but only by the scope of the appended claims.

What is claimed is:

1. A circuit for measuring the conductivity of a blood sample, the circuit including:

a. a first and second connection point, each connection point being configured to be coupled to a blood conductivity sensor and the second connection point also being configured to be coupled to a drive signal source;

b. a half-wave rectifier coupled to the first connection point; and c. an integrator coupled to the output of the half-wave rectifier.

2. A circuit for measuring the conductivity of a blood sample in order to determine the hematocrit of the blood sample, the circuit including:

a. a first, second, and third connection point, the first and second connection point being configured to be coupled to a first and second electrode of a blood conductivity sensor, the third connection point being configured to be coupled to a drive signal source;

b. a half-wave rectifier coupled to the first connection point;

c. an integrator coupled to the output of the half-wave rectifier; and d. a filter coupled between the second and third connection point.

3. The circuit of claim 2, wherein an impedance matching circuit is provided between the filter and the third connection point.

4. The circuit of claim 2, wherein an impedance matching circuit is provided between the filter and the second connection point.

5. The circuit of claim 2, wherein a coupling capacitor is provided between the filter and the third connection point.

6. The circuit of claim 2, wherein the filter is a 4-pole filter.

7. The circuit of claim 2, wherein the integrator includes:

(a) an operational amplifier having a non-inverting input, an inverting input, and an output;

(b) a capacitor coupled between the inverting input and the output; and (c) a resistor coupled between the inverting input and the output in parallel with the capacitor.

8. The circuit of claim 2, wherein the rectifier includes:

a. a first and second switch, each having a signal input, a signal output, and a control input signal, the signal inputs of the first and second switch being coupled together, the output of the first switch being coupled to ground, and the output of the second switch being coupled to the input of the integrator; and wherein the control input signal to each switch is synchronized to an output drive signal generated by the drive signal source, and the control input signal coupled to the first switch is 180 degrees out-of-phase with the control input signal coupled to the second switch in order to couple the integrator to the hematocrit sensor when current flows in a first direction through the hematocrit sensor and to alternatively disconnect the integrator from the hematocrit sensor and couple the hematocrit sensor to ground when current flows in a second direction through the hematocrit sensor.

9. The circuit of claim 8, wherein a phase difference between the output drive signal and the control input signal coupled to the first switch is essentially equal to the phase shift imposed on a signal after the signal passes through the filter.

10. The circuit of claim 2, wherein a drive signal is provided by the drive signal source.

11. The circuit of claim 10, wherein the drive signal is a 10.8 kHz square wave signal.

12. The circuit of claim 11, wherein the drive signal source divides an 11.0592 MHz signal by 1024 to derive the 10.8 kHz square wave signal.

13. The circuit of claim 12, wherein the drive signal source includes a programmable logic device for performing the division which generates the 10.8 kHz square wave signal.

14. The circuit of claim 2, further including a switch coupled between the filter and the second connection point.

15. The circuit of claim 14, further including a control device coupled to a control input to the switch for generating an enable signal to control operation of the switch.

16. A method for measuring hematocrit of a blood sample, including the steps of:
 a. generating an output drive signal;
 b. coupling the output drive signal to a first electrode of a blood conductivity sensor;
 c. coupling a second electrode of the blood conductivity sensor to a half-wave rectifier;
 d. coupling the output from the half-wave rectifier to an integrator;
 e. reading the output from the integrator while the blood conductivity electrodes are emersed in a calibrant;
 f. reading the output from the integrator while the blood conductivity electrodes are emersed in a blood sample; and
 g. determining the hematocrit value of the blood sample by generating a ratio $\phi$ of the integrator output read when the blood conductivity sensor electrodes were emersed in the blood sample with respect to the integrator output read when the blood conductivity sensor electrodes were emersed in the calibrant and applying the ratio $\phi$ to the formula:

$$H = a \ln \phi - b;$$

where H is the hematocrit value of the blood sample, a is a first known cell constant, and b is a second known cell constant.

17. The method of claim 16, wherein the output drive signal is a square wave signal, and further including the step of shaping the square wave output drive signal into a sinusoidal signal prior to coupling the output drive signal to the blood conductivity sensor.

18. The method of claim 17, further including the step of:
 a. synchronizing the half-wave rectifier to the output drive signal such that the second blood conductivity sensor electrode is coupled to the integrator during a negative current phase, and to ground during a positive current phase.

* * * * *